US011384366B2

(12) United States Patent
Qin et al.

(10) Patent No.: US 11,384,366 B2
(45) Date of Patent: Jul. 12, 2022

(54) LENTIVIRAL VECTOR CAPABLE OF DIRECTLY REFLECTING TYPE I INTERFERON RESPONSE, PREPARATION METHOD THEREOF, AND APPLICATIONS THEREOF

(71) Applicant: Fantasia Biopharma (Zhejiang) Co. Ltd., Jinhua (CN)

(72) Inventors: Frank XiaoFeng Qin, Sugar Land Houston, TX (US); Fei Wu, Jiangsu (CN); Zining Wang, Guangdong (CN); Jingyun Ji, Guangdong (CN); Jing Xia, Jiangsu (CN)

(73) Assignee: Fantasia Biopharma (Zhejiang) Co. Ltd., Jinhua (CN)

( * ) Notice: Subject to any disclaimer, the term of this patent is extended or adjusted under 35 U.S.C. 154(b) by 196 days.

(21) Appl. No.: 16/092,796

(22) PCT Filed: Mar. 29, 2017

(86) PCT No.: PCT/CN2017/078646
§ 371 (c)(1),
(2) Date: Oct. 11, 2018

(87) PCT Pub. No.: WO2017/177826
PCT Pub. Date: Oct. 19, 2017

(65) Prior Publication Data
US 2019/0119700 A1 Apr. 25, 2019

(30) Foreign Application Priority Data

Apr. 11, 2016 (CN) .......................... 201610220345.7

(51) Int. Cl.
| C12N 15/79 | (2006.01) |
| C07H 21/04 | (2006.01) |
| C12N 15/867 | (2006.01) |
| C12N 15/65 | (2006.01) |
| C12N 15/86 | (2006.01) |
| C12Q 1/66 | (2006.01) |

(52) U.S. Cl.
CPC .......... *C12N 15/867* (2013.01); *C12N 15/65* (2013.01); *C12N 15/86* (2013.01); *C12Q 1/66* (2013.01); *C07H 21/04* (2013.01); *C12N 2320/30* (2013.01); *C12N 2740/10041* (2013.01); *C12N 2740/16043* (2013.01); *C12N 2799/04* (2013.01)

(58) Field of Classification Search
CPC ................. C12N 15/86; C12N 15/867; C12N 2740/10041; C07H 21/04
See application file for complete search history.

(56) References Cited

U.S. PATENT DOCUMENTS 6,232,107 B1   5/2001 Bryan et al.

FOREIGN PATENT DOCUMENTS

CN  105861559 A  8/2016

OTHER PUBLICATIONS

Wang, Zining et al.: "Complex Regulation Pattern of IRF3 Activation Revealed by a Novel Dimerization Reporter System", The Journal of Immunology, 2016, 196, pp. 4322-4330.
Cassonnet, Patricia et al.: "Benchmarking a luciferase complementation assay for detecting protein complexes", Nature Methods, vol. 8, No. 12, Dec. 2011, pp. 990-992.
Remy, Ingrid et al.: "A highly sensitive protein-protein interaction assay based on Gaussia luciferase", Nature Methods, vol. 3, No. 12, Dec. 2006, pp. 977-979.
Wu, Jiaxi et al.: "Innate Immune Sensing and Signaling of Cytosolic Nucleic Acids", Annual Review of Immunology, 2014, 32, pp. 461-488.
Yan, Nan et al.: "Intrinsic antiviral immunity", Nature Immunology, vol. 13, No. 3, Mar. 2012, pp. 214-222.
Fu, Xin-Yuan et al.: "ISGF3, the transcriptional activator induced by interferon α, consists of multiple interacting polypeptide chains", Proceedings of the National Academy of Sciences USA, vol. 87, Nov. 1990, pp. 8555-8559.
Liu, Su-Yang et al.: "Systematic identification of type I and type II interferon-induced antiviral factors", PNAS, vol. 109, No. 11. Mar. 13, 2012, pp. 4239-4244.
Tamura, Tomohiko et al.: "The IRF Family Transcription Factors in Immunity and Oncogenesis", Annual Review of Immunology, 2008, 26, pp. 535-584.
Wu, Jiaxi et al.: "Cyclic GMP-AMP is an Endogenous Second Messenger in Innate Immune Signaling by Cytosolic DNA", Science, vol. 339, Feb. 15, 2013, pp. 826-830.
Ishikawa, Hiroki et al.: "STING is an endoplasmic reticulum adaptor that facilitates innate immune signalling", Nature, vol. 455, Oct. 2008, pp. 674-678, including full methods and correction.
Kumar, Himanshu et al.: "Pathogen Recognition by the Innate Immune System", International Reviews of Immunology, 30, 2011, pp. 16-34.

(Continued)

*Primary Examiner* — Shin Lin Chen
(74) *Attorney, Agent, or Firm* — McCarter & English, LLP

(57) ABSTRACT

Provided are a method for establishing a lentiviral vector system capable of directly reflecting type I interferon response, and applications thereof. The method for establishing the lentiviral vector system comprises: cutting a *Gaussia* luciferase at the position of amino acid 109, removing 16 amino acids from N-terminus, and cloning the two polypeptides into a lentiviral vector to form a lentiviral BiLC expression vector; and cloning a shuttle plasmid of pEntry-IRF3 or pEntry-IRF5 or pEntry-IRF7 by homologous recombination into the lentiviral BiLC expression vector, so as to construct a lentiviral vector IRF3-BiLC or IRF5-BiLC or IRF7-BiLC capable of directly reflecting type I interferon response.

2 Claims, 3 Drawing Sheets

Specification includes a Sequence Listing.

(56) References Cited

OTHER PUBLICATIONS

Honda, Kenya et al.: "IRF-7 is the master regulator of type-I Interferon-dependent immune responses", *Nature*, vol. 434, Apr. 7, 2005, pp. 772-777.
Zhang, Zhiqiang et al.: "The helicase DDX41 senses intracellular DNA mediated by the adaptor STING in dendritic cells" Supplementary File to *Nature Immunology*, 12, 2011, pp. 959-965.
Jin, Shu et al.: "Progress of interferon regulatory factor 5", *International Journal of Pediatrics*, vol. 42, No. 1, Jan. 31, 2015, pp. 28-30 and 34, in Chinese with English abstract.
He, Jingtang et al.: "Study Advance on Construction and Action of Interferon Regulatory Factor 7", *Chinese Journal of Misdiagnostics*, vol. 10, No. 25, Sep. 30, 2010, pp. 6063 and 6065, in Chinese with English abstract.
Chen, Jianzhong et al: "Progress of interferon regulatory factor 3", *International Journal of Epidemiology and Infectious Disease*, vol. 30, No. 4. Aug. 31, 2003, pp. 223-226, in Chinese with English abstract.
International Search Report and Written Opinion prepared by the Chinese Patent Office, acting as the ISA, for corresponding international application PCT/CN2017/078646 dated Jul. 11, 2017.
Tannous, Bakhos A. et al.: "Codon-Optimized *Gaussia* Luciferase cDNA for Mammalian Gene Expression in Culture and in Vivo," *Molecular Therapy*, vol. 11, No. 3, Mar. 2005, pp. 435-443.
Verhaegen, Monique et al.: "Recombinant *Gaussia* Luciferase, Overexpression, Purification, and Analytical Application of a Bioluminescent Reporter for DNA Hybridization", *Analytical Chemistry*, vol. 74, No. 17, Sep. 1, 2002, pp. 4378-4385.
Szent-Gyorgyi, Christopher et al.: "Cloning and characterization of new bioluminescent proteins", *SPIE*, vol. 3600, Jan. 1999, pp. 4-11.
Remy, Ingrid, et al.: "A highly sensitive protein-protein interaction assay based on *Gaussia* Luciferase" with supplemental figures and supplementary methods, *Nature Methods*, vol. 3, No. 12, Dec. 2006, pp. 977-979 plus supplemental figures and methods (7 pages).

LENTIVIRAL VECTOR CAPABLE OF DIRECTLY REFLECTING TYPE I INTERFERON RESPONSE, PREPARATION METHOD THEREOF, AND APPLICATIONS THEREOF

CROSS-REFERENCE TO RELATED APPLICATIONS

This application is the National Stage entry under 35 U.S.C. § 371 of International Application Number PCT/CN2017/078646 filed on Mar. 29, 2017, published on Oct. 19, 2017 under publication number WO 2017/177826 A1, which claims the benefit of priority under 35 U.S.C. § 119 of Chinese patent application number 201610220345.7 filed Apr. 11, 2016.

SEQUENCE LISTING

The instant application contains a Sequence Listing which has been submitted electronically in ASCII format and is hereby incorporated by reference in its entirety. Said ASCII copy, created on Jul. 22, 2021, is named 127648-00201_SL.txt and is 16,791 bytes in size.

TECHNICAL FIELD

The present disclosure relates to a lentiviral vector capable of directly reflecting type I interferon response, preparation method thereof, and applications thereof, and belongs to the field of pharmaceutical technology.

BACKGROUND

Human bodies suffering from viruses infections such as influenza virus, hepatitis C virus, herpes virus infections and the like, as well as bacterial or fungal infections, or the metastasis of cancer cells in tumor patients may cause innate immunity and adaptive immunity of the body[1]. Among them, the innate immune response exerts antiviral effects mainly by inducing the production of interferon (IFN) and activating the downstream interferon-stimulated genes (ISGs)[2, 3]. For RNA viruses, such as influenza virus and hepatitis C virus, the viruses invade into cells, and the released RNA can be recognized by the intracellular RNA recognition receptors such as RIG-I, MDA5 and the like, and then recruits the IPS-1 protein and phosphorylated kinase proteins on mitochondria. The phosphorylated kinase proteins may cause the phosphorylation and dimer formation of proteins including IRF3, IRF5, and IRF7 proteins, so as to enter cell nucleus and cause the production of interferon[4].

For DNA viruses, such as herpes virus and adenovirus, the DNA released by the viruses after they enter the body can be recognized by DNA recognition receptors such as DDX41, cGAS, IFI16 and the like, and induces the polymerization of STING, so as to cause the phosphorylation of kinases and the activation of IRF3 dimers, which further cause the transcription and translation of interferon[5-7]. For bacterial infections, the interferon response reaction is mainly caused by recognizing the LPS substance of bacteria by TLR4 recognition receptors on cell membrane and causing the activation of the dimers of the downstream TRIF, TRAF6, TBK1 and IRF3, IRF5, IRF7. The produced interferon may enable cells to eliminate the invading RNA viruses or DNA viruses by inducing the expression of ISGs. Therefore, the interferon response is extremely important in the infection processes of viruses and bacteria. In order to better and effectively resist the invasion of viruses and bacteria and eliminate them, studying the regulation mechanism of the interferon response is particularly important.

At present, the interferon-stimulated response element luciferase reporter plasmid (ISRE-Luc) is the main reporter system for investigating the mechanism of interferon production. ISRE-Luc has a reaction process that mimics cell genome. ISRE-Luc possesses an ISRE promoter with the same sequence as the promoter of the genome, and has an expression gene of a full-length humanized firefly luciferase linked after the promoter. When cells suffer from viral or bacterial infections, ISRE-Luc can cause the interferon response reaction in the cells and activate the transcription of ISRE, so as to cause the transcription, translation and expression of the luciferase gene. Therefore, the intensity of the intracellular interferon response reaction may be reflected by detecting the activity of firefly luciferase. Currently, this is mainly used for studying and screening the regulation mechanisms of certain protein molecules or drugs on the interferon response.

However, the activation of ISRE transcription can be recognized by IRF3 dimers and IRF7 dimers, and the transcription may occur[8]. Meanwhile, the interferon produced by the transcription and translation can reactivate and amplify the interferon recognition receptors (IFNAR1, etc.), causing the formation of STAT1/STAT2/IRF3 (ISGF3) trimer, and ISRE can be recognized, which leads to transcription)[9,10]. Therefore, ISRE-Luc cannot specifically and precisely reflect the regulation mechanism of interferon within cells. Secondly, the secondary amplification of ISRE needs to rely on the interferon recognition receptors (IFNAR1, etc.) of cells. Therefore, it is not suitable for detecting the regulation mechanism of interferon in cells under the conditions that the activities are affected, such as conditions in which IFNAR1 or STAT1 is knocked out. Thirdly, ISRE-Luc requires certain level of transcription and translation, and cannot reflect well the regulation of the interferon response at transcriptional or translational level by certain molecules or drugs.

In summary, a reporter system of the interferon response reaction, which is specific, sensitive, direct, and can be widely used, will have broad application prospects.

The literatures mentioned in the above background art specifically refer to the following respectively:

(1) Wu, J., and Z. J. Chen. 2014. Innate immune sensing and signaling of cytosolic nucleic acids. Annual review of immunology 32:461-488.

(2) Yan, N., and Z. J. Chen. 2012. Intrinsic antiviral immunity. Nat Immunol 13:214-222.

(3) Kumar, H., T. Kawai, and S. Akira. 2011. Pathogen recognition by the innate immune system. International reviews of immunology 30:16-34.

(4) Tamura, T., H. Yanai, D. Savitsky, and T. Taniguchi. 2008. The IRF family transcription factors in immunity and oncogenesis. Annual review of immunology 26:535-584.

(5) Zhang, Z. Q., B. Yuan, M. S. Bao, N. Lu, T. Kim, and Y. J. Liu. 2012. The helicase DDX41 senses intracellular DNA mediated by the adaptor STING in dendritic cells (vol 12, pg 959, 2011). Nat Immunol 13:196-196.

(6) Wu, J. X., L. J. Sun, X. Chen, F. H. Du, H. P. Shi, C. Chen, and Z. J. J. Chen. 2013. Cyclic GMP-AMP Is an Endogenous Second Messenger in Innate Immune Signaling by Cytosolic DNA. Science 339:826-830.

(7) Ishikawa, H., and G N. Barber. 2009. Sting is an endoplasmic reticulum adaptor that facilitates innate immune signaling. Cytokine 48:128-128.

(8) Honda, K., H. Yanai, H. Negishi, M. Asagiri, M. Sato, T. Mizutani, N. Shimada, Y Ohba, A. Takaoka, N. Yoshida, and T. Taniguchi. 2005. IRF-7 is the master regulator of type-I interferon-dependent immune responses. Nature 434: 772-777.

(9) Liu, S. Y, D. J. Sanchez, R. Aliyari, S. Lu, and G. Cheng. 2012. Systematic identification of type I and type II interferon-induced antiviral factors. Proceedings of the National Academy of Sciences of the United States of America 109:4239-4244.

(10) Fu, X. Y, D. S. Kessler, S. A. Veals, D. E. Levy, and J. E. Darnell, Jr. 1990. ISGF3, the transcriptional activator induced by interferon alpha, consists of multiple interacting polypeptide chains. Proceedings of the National Academy of Sciences of the United States of America 87:8555-8559.

SUMMARY

An object of the present disclosure is to solve the above-mentioned technical problems, and to provide a BiLC reporter system which is mediated by the interferon regulatory factor family and reflects type I interferon response sensitively, specifically and directly.

The technical solutions of the present disclosure are: a lentiviral vector capable of directly reflecting type I interferon response, wherein *Gaussia* luciferase is cleaved at a position of amino acid 109 into two polypeptides of N-terminus and C-terminus, and 16 amino acids at the N-terminus are removed. The two polypeptides are denoted as GlucN and GlucC and are cloned into the lentiviral vector to form a lentiviral BiLC expression vector; then a shuttle plasmid of pEntry-IRF3 or pEntry-IRF5 or pEntry-IRF7 is cloned by homologous recombination into the above-mentioned lentiviral BiLC expression vector, so as to construct a lentiviral vector IRF3-BiLC or IRF5-BiLC or IRF7-BiLC capable of directly reflecting type I interferon response.

In the above-mentioned lentiviral vector capable of directly reflecting type I interferon response, it is guaranteed that the amino acid sequence encoded by the IRF3 or IRF5 or IRF7 gene in the pEntry-IRF3 or pEntry-IRF5 or pEntry-IRF7 has a sequence homology of not less than 80% with NP 001184051.1 (MGTPKPRILPWLVSQLD-LGQLEGVAWVNKSRTRFRIPWKHGLRQDAQQEDF-GIFQA WAEATGAYVPGRDKPDLPTWKRNFRSAL-NRKEGLRLAEDRSKDPHDPHKIYEFVNSG VGDFSQPDTSPDTNGGGSTSDTQEDILDELLGNMV-LAPLPDPGPPSLAVAPEPCPQPLR SPSLDNPTPFPNLGPSENPLKRLLVPGEEWEFE-VTAFYRGRQVFQQTISCPEGLRLVGSE VGDRTLPGWPVTLPDPGMSLTDRGVM-SYVRHVLSCLGGGLALWRAGQWLWAQRLG HCHTY-WAVSEELLPNSGHGPDGEVPKDKEG-GVFDLGPFIVGSWAPRSDYLHGRKRTL TTLCPLVLCGGVMAPGPAVDQEARDGQGCAHVPQG LGRNGPGRGCLLPGEYCGPAH FQQPPTL-PHLRPVQGLPAGLGGGHGFPGPWGELSPRSS-WCASNPPVPHHLNQ (SEQ ID NO: 7)) or NP_001092097.2 MNQSIPVAPTP-PRRVRLKPWLVAQVNSCQYPGLQWVNGEKKLFCIP-WRHATRHGP SQ DGDNTIFKAWA-KETGKYTEGVDEADPAKWKANLRCALNKSRDFRLI YDGPRDMPPQ PYKI-YEVCSNGPAPTDSQPPEDYSFGAGEEEEEEEELQRML PSLSLTEDVKWPPTLQPP TLRPPTLQPPTLQPPVVLGPPAPDPSPLAPPPGNPAG-FRELLSEVLEPGPLPASLPPAGEQ LLPDL-LISPHMLPLTDLEIKFQYRGRPPRALTIS-NPHGCRLFYSQLEATQEQVELFGPISL EQVRFPSPEDIPSDKQRFYTNQLLDVLDRGLI-LQLQGQDLYAIRLCQCKVFWSGPCASA HDSCPN-PIQREVKTKLFSLEHFLNELILFQKGQTNTPPPFE-IFFCFGEEWPDRKPREKKLI TVQVVPVAARLLLEMFSGELSWSADSIRLQIS-NPDLKDRMVEQFKELHHIWQSQQRLQ PVAQAPP-GAGLGVGQGPWPMHPAGMQ (SEQ ID NO: 8)) or NP_001563.2 MALAPERAAPRVLFGEWLLGEIS-SGCYEGLQWLDEARTCFRVPWKHFARKDLSEADA RIFKAWAVARGRWPPSSRGGGPPPEAETAER-AGWKTNFRCALRSTRRFVMLRDNSGD PADPHKVY-ALSRELCWREGPGTDQTEAEAPAAVPPPQGGPPGP-FLAHTHAGLQAPGP LPAPAGDKGDLLLQAVQQSCLADHLLTASW-GADPVPTKAPGEGQEGLPLTGACAGGP GLPAGE-LYGWAVETTPSPGPQPAALTTGEAAAPESPHQAE-PYLSPSPSACTAVQEPSPG ALDVTIMYKGRTVLQKVVGHPSCTFLYGPPD-PAVRATDPQQVAFPSPAELPDQKQLR YTEELLRHVAPGLHLELRGPQLWARRMGKCKVYW-EVGGPPGSASPSTPACLLPRNCD TPIFD-FRVFFQELVEFRARQRRGSPRYTIYLGFGQDL-SAGRPKEKSLVLVKLEPWLCRV HLEGTQREGVSSLDSSSLSLCLSSANSLYDD-IECFLMELEQPA (SEQ ID NO: 9)), respectively, and the gene sequence of the IRF3-BiLC or IRF5-BiLC or IRF7-BiLC vector is kept consistent with the gene sequence corresponding to IRF3 or IRF5 or IRF7.

The lentiviral vector of the present disclosure may be used for constructing a cell line which induces the body to directly reflect type I interferon response when the body is infected by viruses, bacteria, fungus, and other microorganisms. The lentiviral vector of the present disclosure may also be used for constructing a cell line which induces the body to generate innate immune response under the conditions of chronic inflammations caused by autoimmune system disorders of the body and a series of microenvironments of tumor tissues. The constructed cell line may be: a THP-1 (IRF3-BiLC) cell line, a THP-1 (IRF5-BiLC) cell line, a THP-1 (IRF7-BiLC) cell line, or a THP-1-Dual cell line. The method for constructing the cell line is as follows:

S1. Construction of plasmids: IRF3, IRF5, or IRF7 gene is amplified by a specific primer, and a double enzyme digestion of the amplified products is performed, followed by ligation to a vector by T4 ligase, and the shuttle plasmid of a full-length pEntry-IRF3, pEntry-IRF5, or pEntry-IRF7 is extracted;

S2. Construction of a lentiviral expression vector: GlucN and GlucC portions are adopted and are cloned into the lentiviral vector respectively;

S3. Construction of the lentiviral vector capable of directly reflecting type I interferon response: the constructed shuttle plasmid of the full-length pEntry-IRF3, pEntry-IRF5, or pEntry-IRF7 is homologously recombined into the inducible lentiviral expression vector formed in S2 by cloning technology to form pBiLC-IRF3-GlucN and pBiLC-IRF3-GlucC, or pBiLC-IRF5-GlucN and pBiLC-IRF5-GlucC, or pBiLC-IRF7-GlucN and pBiLC-IRF7-GlucC, which express IRF3-GlucN fusion protein and IRF3-GlucC fusion protein, or IRF5-GlucN fusion protein and IRF5-GlucC fusion protein, or IRF7-GlucN fusion protein and IRF7-GlucC fusion protein respectively;

S4. Construction of a cell line stably expressing IRF3-BiLC, IRF5-BiLC or IRF7-BiLC: the IRF3-GlucN fusion protein-expressing vector and the IRF3-GlucC fusion protein-expressing vector, or the IRF5-GlucN fusion protein-expressing vector and the IRF5-GlucC fusion protein-expressing vector, or the IRF7-GlucN fusion protein-expressing vector and the IRF7-GlucC fusion protein-expressing vector are integrated into the corresponding cell lines by a pMDLg/pRRE, pRSV-Rev, pMD2.G three-plasmid system;

wherein the sequence of the specific primer used for the amplification of the IRF3, IRF5 or IRF7 gene in S1 is SEQ ID NO:1, SEQ ID NO:2, SEQ ID NO:3, SEQ ID NO:4, SEQ ID NO:5, or SEQ ID NO:6.

Preferably, in the above construction process, the amplification condition of the IRF3, IRF5, or IRF7 gene in step S1 is: pre-denaturation at 95° C. for 2 min; followed by 30 cycles, and the condition of each cycle is denaturation at 95° C. for 20 s, annealing at 56° C. for 30 s, elongation at 72° C. for 1 min; and lastly, elongation at 72° C. for 5 min.

"IRF3-GlucN and IRF3-GlucC", "IRF5-GlucN and IRF5-GlucC", or "IRF7-GlucN and IRF7-GlucC" of the constructed IRF3-BiLC, IRF5-BiLC, or IRF7-BiLC reporter system are based on a lentiviral vector system, which may be used either as a stable transfection system or as a transient transfection system.

The beneficial effects of the present disclosure are mainly reflected in the following two aspects:

Firstly, compared to the currently used reporter system for type I interferon response, the IRF-BiLC reporter system can specifically reflect type I interferon response.

Secondly, the IRF-BiLC reporter system is capable of directly and rapidly reflecting the transient or persistent type I interferon response.

DETAILED DESCRIPTION

Figure 1:
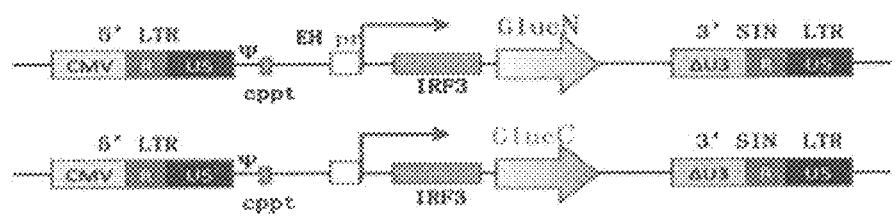
FIG. 1 is a schematic diagram of the structure of a constructed IRF-BiLC plasmid.

The present disclosure specifically discloses a reporter cell line that specifically, sensitively, and directly reflects type I interferon response, and a construction method and the specific application of the reporter cell line. The technical solution of the present disclosure is described in detail as follows.

1. Construction of IRF3-BiLC, IRF5-BiLC, or IRF7-BiLC Lentiviral Vector

The principle of BiLC is as follows: Gaussia luciferase is cleaved at a specific site to form two polypeptides of N-terminus and C-terminus without luciferase activity, which are denoted as N-fragment and C-fragment (Remy and Michnick, 2006; Cassonnet et al., 2011; Tannous et al., 2005). When these two fragments are co-expressed in cells or mixed in vitro, they cannot be assembled spontaneously into active luciferase proteins. However, when the fragments of these two luciferase proteins are respectively linked to a group of target proteins having interactions and co-expressed in cells or the two fusion proteins are mixed in vitro, due to the interactions of the target proteins, the two fragments of the luciferase protein are spatially close to each other and complement each other, and are reconstituted into a complete and active luciferase protein molecule that emits fluorescence with coelenterazine (CTZ) as substrate under the condition of CTZ as substrate. In short, if there are interactions between the target proteins, there will be fluorescence produced by luciferase with CTZ as substrate; on the contrary, if there is no interaction between the proteins, there will be no luciferase activity. Gaussia luciferase having the nucleic acid sequence, aagcccaccgagaacaacgaggactt-caacatcgtggccgtggccagcaacttcgccaccaccgacctggacgccga-taggggcaa
actgccagggaagaagctgcccctggaggtgctgaaagagatggaggc-caacgccaggaaggccggctgcacaagaggctgtctg atctgcctgagcca-catcaagtgcaccccaagatgaagaagttcatccccggcaggtgtcacacc-tacgagggcgacaaagagagc
gcccagggcggcatcggcgaggccatcgtggacatccccgagatccccggctt-caaggacctggagcccatggagcagttcatcgcc caggtg-gatctgtgcgtggactgcaccaccggctgcctgaagggcctggc-caatgtgcaatgcagcgacctgctgaagaaatggctgc
cccagaggtgcgccaccttcgccagcaagatccagggccaagtggacaagat-caaggggctggggggggac (SEQ ID NO: 10), encoding the amino acid sequence, KPTENNEDFNIVAVASNFATTDL-DADRGKLPGKKLPLEVLKEMEANARKAGCTRGCLI CLSHIKCTPKMKKFIPGRCHTYEGDKESAQG-GIGEAIVDIPEIPGFKDLEPMEQFIAQVD LCVDCTTGCLKGLANVQCSDLLKKWLPQR-CATFASKIQGQVDKIKGAGGD (SEQ ID NO: 11), was cleaved into N-terminus and C-terminus at a position of amino acid 109, and 16 amino acids at the N-terminus were removed. The two polypeptides were denoted as GlucN and GlucC respectively. Humanized GlucC and GlucN gene fragments synthesized by Shanghai Generay Biotech Co., Ltd. entered a lentiviral vector (US20120201794 A1) by T4 ligase (purchased from NEB) via AscI and RsrII (purchased from NEB) restriction sites, denoted as pBiLC1-2.

On the other hand, the IRF3, IRF5, and IRF7 genes are all members of the interferon regulatory factor family, and their structures and functions have a certain degree of similarity. A variant of the amino acid sequence of IRF3 or IRF5 or IRF7 of the present disclosure may be a substitution variant, an insertion variant or a deletion variant. As compared to the wild-type or unaltered polypeptides or other reference polypeptides, mutations in the genes encoding the polypeptides may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450 or more non-contiguous or contiguous amino acids (i.e., segments) of the polypeptides.

According to the technical solution of the present disclosure, the IRF3 (NM_001197122.1), IRF5 (NM_001098627.3), and IRF7 (NM_001572.3) genes were amplified by designing specific primers and using cDNA of cells of human origin as a template. Said amplification condition was: pre-denaturation at 95° C. for 2 min; followed by 30 cycles, and the condition of each cycle was denaturation at 95° C. for 20 s, annealing at 56° C. for 30 s, elongation at 72° C. for 1 min; and lastly, elongation at 72° C. for 5 min. The above-mentioned primer sequences are shown in Table 1.

TABLE 1

Primer sequences

| | | |
|---|---|---|
| SEQ ID NO: 1 | PA-F | ATAGCGGCCGCAATGGGAACCCCAAAGCC |
| SEQ ID NO: 2 | PA-R | GGCGCGCCCTTGGTTGAGGTGGTGGGG |
| SEQ ID NO: 3 | PA-F | ATAGCGGCCGCAATGAACCAGTCCATCC |
| SEQ ID NO: 4 | PA-R | GGCGCGCCCCTTTTTATTGCATGCCAG |
| SEQ ID NO: 5 | PA-F | ATAGCGGCCGCAATGGCCTTGGCTCCTG |
| SEQ ID NO: 6 | PA-R | GGCGCGCCCTTCTAGGCGGGCTGCTCC |

PCR products and a pEntry vector (purchased from the Invitrogen Corporation) were double digested with NotI and AscI (purchased from the NEB Corporation), and the fragments were ligated to the pEntry vector using T4 ligase (purchased from the NEB Corporation). After verification by sequencing, plasmids were extracted, preserved and denoted as pEntry-IRF3, pEntry-IRF5, and pEntry-IRF7. By Gateway cloning technology, pEntry-IRF3, pEntry-IRF5, and pEntry-IRF7 were cloned into the lentiviral BiLC expression vectors to obtain pBiLC-IRF3-GlucN and pBiLC-IRF3-GlucC, pBiLC-IRF5-GlucN and pBiLC-IRF5-GlucC, or pBiLC-IRF7-GlucN and pBiLC-IRF7-GlucC, which express the fusion proteins of IRF3-GlucN and IRF3-GlucC, IRF5-GlucN and IRF5-GlucC, or IRF7-GlucN and IRF7-GlucC, respectively. The constructed plasmid was exemplified by pEntry-IRF3, as shown in FIG. 1.

2. Detection of the Responses of IRF3-BiLC and the Like to Different Stimulations THP-1 cell line stably expressing IRF3-BiLC, IRF5-BiLC, or IRF7-BiLC was constructed. The specific operation steps were as follows with IRF3-BiLC as an example:

a. Lentiviral packaging: One day before transfection, HEK293T cells (ATCC: CRL-11268) were plated in a 24-well plate (purchased from the Thermo Corporation) in 500 μL of DMEM (purchased from Invitrogen) complete culture medium (10% FBS, purchased from Gibco); transfection was performed when the cells reached a density of 50%-60%, and about 1 μg of plasmid in total was used for transfection in each well, wherein:

pMDLg/pRRE:pRSV-Rev:pMD2.G:IRF3-GlucN/IRF3-GlucC=4:2:1:2.

After 8 h of transfection, the culture medium was removed, and 1 mL of fresh culture medium was supplemented. After 48 h, the supernatant was collected into an EP tube and centrifuged at 2500 rpm for 4 min. The supernatant was transferred into a new EP tube for virus invasion.

b. Virus invasion: 18 h before virus collection, 10,000 THP-1 cells (Invivogen) were plated in a 96-well plate (purchased from the Thermo Corporation) using 100 μL of DMEM. Before invasion, approximately 50 μL of RMPI 1640 was removed. 6 μg/mL of polybrene (purchased from Sigma) was added into the collected supernatant of the virus solution, mixed well, and about 100 μL of virus solution was added into each well of the 96 wells. After 6-8 h of invasion, 50 μL of the culture medium in each wells of the 96 wells was removed, and 100 μL of fresh culture medium was added. After 72 h, the cells could be transferred out of the 96-well plate for screening and expansion culture, thus a THP-1 (IRF3-BiLC) cell line was obtained.

The obtained THP-1 (IRF3-BiLC) cell line was used to test the luciferase activities formed by the dimerization of IRF3, IRF5, and IRF7 under different stimulations. TNF, IL-1B, LPS, polyI:C, polydA:dT, and VSV-EGFP were used for stimulation, respectively. Lysis was performed on ice for 10 min using 80 μL of *Renilla* luciferase lysate (purchased from Promega, E2820). The mixture was mixed well by a pipette and 50 μL of cell lysate was transferred to a luciferase detector plate (purchased from PE). 20 μL of *Renilla* luciferase substrate (purchased from Promega, E2820) was added per well, and the luciferase activity was detected by a microplate reader (purchased from Bio-Tek, Synergy H1).

Figure 2A:
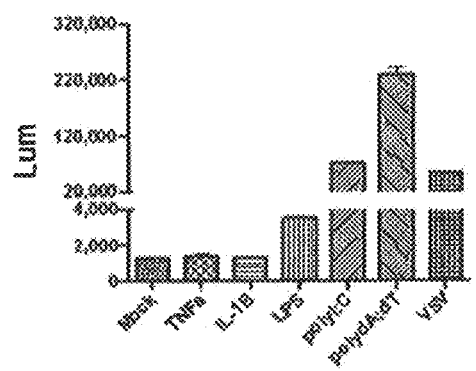
FIG. 2a is a graph illustrating the detected signal values of IRF3 dimers induced by different stimulus conditions in THP-1 (IRF3-BiLC).
Figure 2B:
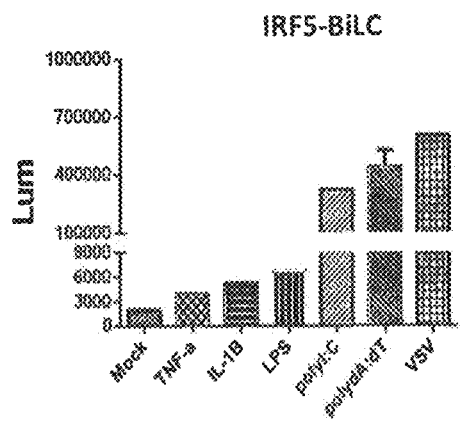
FIG. 2b is a graph illustrating the detected signal values of IRF5 dimers induced by different stimulus conditions in THP-1 (IRF5-BiLC).
Figure 2C:
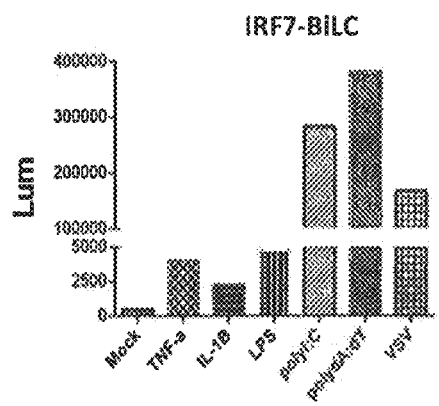
FIG. 2c is a graph illustrating the detected signal values of IRF7 dimers induced by different stimulus conditions in THP-1 (IRF7-BiLC).

Similar to the above-mentioned steps, THP-1 cell lines of IRF5-BiLC and IRF7-BiLC could be constructed, and the results of the dimer formation of IRF3, IRF5, and IRF7 were detected. The results are as shown in FIG. 2a, FIG. 2b, and FIG. 2c. It can be seen from the figures that TNFa and IL-1B cannot cause the formation of the signals of the IRF3, IRF5, and IRF7 dimers, while LPS, polyI:C, polydA:dT, and VSV-eGFP may cause the signals of the IRF3, IRF5, and IRF7 dimers to varying degrees.

3. Detection of the Specificity of IRF3-BiLC to Reflect the Interferon Response Reaction THP-1-Dual (with a stable expression's ISRE-Luc reporter system, purchased from the Invivogen Corporation) or THP-1 (IRF3-BiLC) cells were plated in a 24-well plate at a concentration of 1000,000 cells per mL. After 14 hours, transfection was performed. The plated cells were divided into 8 groups. Among them, for four groups of Dual, one group was denoted as NT group, and IFNα (final concentration: 10 ng/mL), IFNβ (final concentration: 10 ng/mL), IFNγ (final concentration: 20 ng/mL) were added into the other three groups respectively; four groups of IRF3-BiLC were treated in the same manner as the four groups of ISRE-Luc. At 24 hours, firefly luciferase (with *Renilla* luciferase as an internal reference) and *Gaussia* luciferase (with firefly luciferase as an internal reference) were detected respectively.

Figure 3:
FIG. 3 is a graph illustrating the detected effects of different IFN stimulations on IRF3-BiLC.
Figure 4:
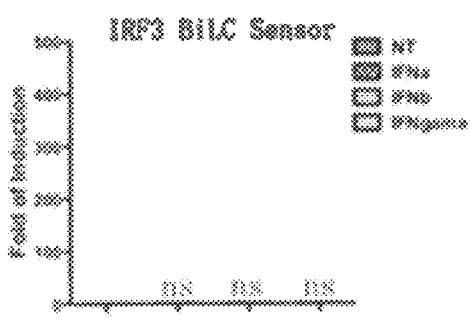
FIG. 4 is a graph illustrating the detected effects of different IFN stimulations on ISRE-Luc.

The results are shown in FIG. 3 and FIG. 4: the IRF3-BiLC groups are not affected by the secondary amplification and activation of interferon, while the ISRE-Luc groups are strongly affected and cannot specifically reflect the induction of type I interferon.

4. Detection of the Universality of the Application of IRF3-BiLC

In order to verify the extensive application of IRF3-BiLC, in the present disclosure, experimental verification was performed in the presence of transcription inhibitors. The details are as follows.

THP-1-Dual (Invivogen) had an ISRE-Luc reporter system with stable expression. THP-1-Dual and THP-1 (IRF3-BiLC) cells were plated at a concentration of 1000,000 cells per mL in a 24-well plate. 4 groups were arranged for THP-1-Dual and THP-1 cells respectively, resulting in a total of 8 groups. After 12 hours, for THP-1-Dual cells, two groups of cells were transfected with Lipo2000 and stimulated with 5 mg/mL of polydA:dT, and the other two groups were not treated. The same treatment was performed for THP-1 (IRF3-BiLC). 4 hours after transfection, for the 2 groups of THP-1-Dual cells that were transfected and stimulated with polydA:dT, CHX with a final concentration of 100 ng/mL was added into one group. For the 2 groups of THP-1-Dual cells that were not treated, CHX with a final concentration of 100 ng/mL was added into one group. The other two groups were not treated. The same treatment was performed for THP-1 (IRF3-BiLC).

After 10 h of CHX treatment, for THP-1-Dual cells, 40 μL of supernatant was taken respectively to detect the luciferase activity. For THP-1 (IRF3-BiLC), 80 μL of *Renilla* luciferase lysate (purchased from Promega, E2820) was used to lyse on ice for 10 min. The mixture was mixed well by a pipette, and 50 μL of cell lysate was transferred to a luciferase detector plate (purchased from PE). 20 μL of *Renilla* luciferase substrate (purchased from Promega, E2820) was added into each well, and the luciferase activity was detected by a microplate reader (purchased from Bio-Tek, Synergy H1).

Figure 5:
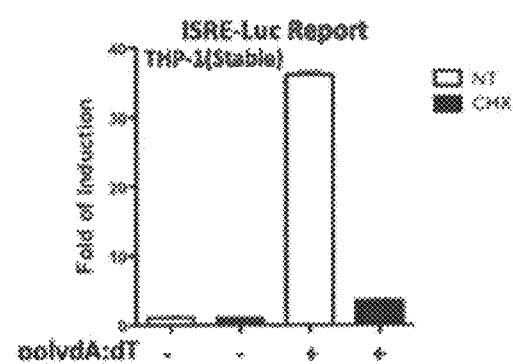
FIG. 5 is a graph illustrating the detected effect of CHX on IRF3-BiLC.
Figure 6:
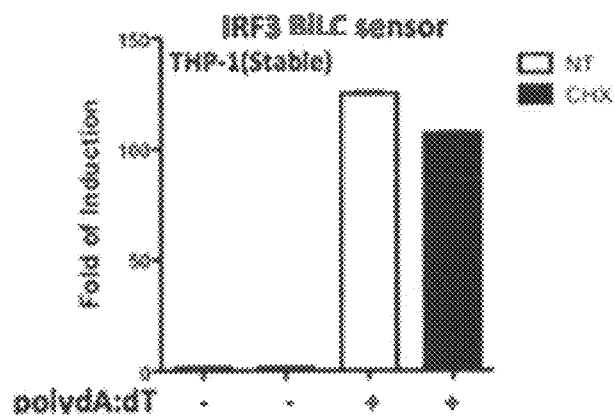
FIG. 6 is a graph illustrating the detected effect of CHX on ISRE-Luc.

The detected values of luciferase were normalized with regard to the untreated groups. The results are as shown in FIG. 5 and FIG. 6: IRF3-BiLC is capable of reflecting the intracellular type I interferon response reaction in the presence of CHX, and ISRE-Luc is affected significantly.

What is claimed is:

1. A lentiviral vector capable of directly reflecting type I interferon response, wherein a *Gaussia* luciferase comprising the amino acid sequence depicted in SEQ ID NO: 11 is cleaved at a position of amino acid 109 of SEQ ID NO: 11 into two polypeptides of N-terminus and C-terminus, and the resulting two polypeptides are respectively denoted as GlucN and GlucC and respective nucleic acid sequences encoding GlucN and GlucC are each cloned into a separate lentiviral vector to form two lentiviral expression vectors denoted BiLC-GlucN and BiLC-GlucC, respectively; then a shuttle plasmid comprising a gene encoding an interferon regulatory factor 3 (IRF3), 5 (IRF5), or 7 (IRF7) protein, wherein the shuttle plasmid is pEntry-IRF3 or pEntry-IRF5 or pEntry-IRF7 is cloned by homologous recombination into the above-mentioned lentiviral BiLC expression vectors to construct lentiviral vectors BiLC-IRF3-GlucN and BiLC-IRF3-GlucC, BiLC-IRF5-GlucN and BiLC-IRF5-GlucC, or BiLC-IRF7-GlucN and BiLC-IRF7-GlucC capable of directly reflecting type I interferon response.

2. The lentiviral vector capable of directly reflecting type I interferon response according to claim 1, wherein it is guaranteed that the amino acid sequence encoded by the IRF3 or IRF5 or IRF7 gene in the pEntry-IRF3 or pEntry-IRF5 or pEntry-IRF7 has a sequence homology of not less than 80% with NP_001184051.1 (SEQ ID NO: 7) or NP_001092097.2 (SEQ ID NO: 8) or NP_001563.2 (SEQ ID NO:9), respectively, and the IRF3, IRF5, and IRF7 gene sequence of the BiLC-IRF3-GlucN and BiLC-IRF3-GlucC, BiLC-IRF5-GlucN and BiLC-IRF5-GlucC, and BiLC-IRF7-GlucN and BiLC-IRF7-GlucC vectors, respectively, is the same as the gene sequence corresponding to IRF3, IRF5, and IRF7 in the pEntry-IRF3, pEntry-IRF5, and pEntry-IRF7 shuttle plasmid, respectively.

* * * * *

SEQUENCE LISTING

```
<160> NUMBER OF SEQ ID NOS: 11

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atagcggccg caatgggaac cccaaagcc                                             29

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggcgcgccct tggttgaggt ggtgggg                                               27

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atagcggccg caatgaacca gtccatcc                                              28

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcgcgccct ttttattgca tgccag                                                26

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atagcggccg caatggcctt ggctcctg                                              28
```

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ggcgcgccct tctaggcggg ctgctcc                                          27

<210> SEQ ID NO 7
<211> LENGTH: 452
<212> TYPE: PRT
<213> ORGANISM: Homo sapiens

<400> SEQUENCE: 7

```
Met Gly Thr Pro Lys Pro Arg Ile Leu Pro Trp Leu Val Ser Gln Leu
1               5                   10                  15

Asp Leu Gly Gln Leu Glu Gly Val Ala Trp Val Asn Lys Ser Arg Thr
            20                  25                  30

Arg Phe Arg Ile Pro Trp Lys His Gly Leu Arg Gln Asp Ala Gln Gln
        35                  40                  45

Glu Asp Phe Gly Ile Phe Gln Ala Trp Ala Glu Ala Thr Gly Ala Tyr
    50                  55                  60

Val Pro Gly Arg Asp Lys Pro Asp Leu Pro Thr Trp Lys Arg Asn Phe
65                  70                  75                  80

Arg Ser Ala Leu Asn Arg Lys Glu Gly Leu Arg Leu Ala Glu Asp Arg
                85                  90                  95

Ser Lys Asp Pro His Asp Pro His Lys Ile Tyr Glu Phe Val Asn Ser
            100                 105                 110

Gly Val Gly Asp Phe Ser Gln Pro Asp Thr Ser Pro Asp Thr Asn Gly
        115                 120                 125

Gly Gly Ser Thr Ser Asp Thr Gln Glu Asp Ile Leu Asp Glu Leu Leu
    130                 135                 140

Gly Asn Met Val Leu Ala Pro Leu Pro Asp Pro Gly Pro Pro Ser Leu
145                 150                 155                 160

Ala Val Ala Pro Glu Pro Cys Pro Gln Pro Leu Arg Ser Pro Ser Leu
                165                 170                 175

Asp Asn Pro Thr Pro Phe Pro Asn Leu Gly Pro Ser Glu Asn Pro Leu
            180                 185                 190

Lys Arg Leu Leu Val Pro Gly Glu Glu Trp Glu Phe Glu Val Thr Ala
        195                 200                 205

Phe Tyr Arg Gly Arg Gln Val Phe Gln Gln Thr Ile Ser Cys Pro Glu
    210                 215                 220

Gly Leu Arg Leu Val Gly Ser Glu Val Gly Asp Arg Thr Leu Pro Gly
225                 230                 235                 240

Trp Pro Val Thr Leu Pro Asp Pro Gly Met Ser Leu Thr Asp Arg Gly
                245                 250                 255

Val Met Ser Tyr Val Arg His Val Leu Ser Cys Leu Gly Gly Gly Leu
            260                 265                 270

Ala Leu Trp Arg Ala Gly Gln Trp Leu Trp Ala Gln Arg Leu Gly His
        275                 280                 285

Cys His Thr Tyr Trp Ala Val Ser Glu Glu Leu Leu Pro Asn Ser Gly
    290                 295                 300

His Gly Pro Asp Gly Glu Val Pro Lys Asp Lys Glu Gly Gly Val Phe
```

```
                305                 310                 315                 320
Asp Leu Gly Pro Phe Ile Val Gly Ser Trp Ala Pro Arg Ser Asp Tyr
                325                 330                 335

Leu His Gly Arg Lys Arg Thr Leu Thr Thr Leu Cys Pro Leu Val Leu
                340                 345                 350

Cys Gly Gly Val Met Ala Pro Gly Pro Ala Val Asp Gln Glu Ala Arg
                355                 360                 365

Asp Gly Gln Gly Cys Ala His Val Pro Gln Gly Leu Gly Arg Asn Gly
        370                 375                 380

Pro Gly Arg Gly Cys Leu Leu Pro Gly Glu Tyr Cys Gly Pro Ala His
385                 390                 395                 400

Phe Gln Gln Pro Pro Thr Leu Pro His Leu Arg Pro Val Gln Gly Leu
                    405                 410                 415

Pro Ala Gly Leu Gly Gly Gly His Gly Phe Pro Gly Pro Trp Gly Glu
                420                 425                 430

Leu Ser Pro Arg Ser Ser Trp Cys Ala Ser Asn Pro Pro Val Pro His
                435                 440                 445

His Leu Asn Gln
    450

<210> SEQ ID NO 8
<211> LENGTH: 498
<212> TYPE: PRT
<213> ORGANISM: Homo sapiens

<400> SEQUENCE: 8

Met Asn Gln Ser Ile Pro Val Ala Pro Thr Pro Arg Arg Val Arg
1               5                   10                  15

Leu Lys Pro Trp Leu Val Ala Gln Val Asn Ser Cys Gln Tyr Pro Gly
                20                  25                  30

Leu Gln Trp Val Asn Gly Glu Lys Lys Leu Phe Cys Ile Pro Trp Arg
            35                  40                  45

His Ala Thr Arg His Gly Pro Ser Gln Asp Gly Asp Asn Thr Ile Phe
    50                  55                  60

Lys Ala Trp Ala Lys Glu Thr Gly Lys Tyr Thr Glu Gly Val Asp Glu
65                  70                  75                  80

Ala Asp Pro Ala Lys Trp Lys Ala Asn Leu Arg Cys Ala Leu Asn Lys
                85                  90                  95

Ser Arg Asp Phe Arg Leu Ile Tyr Asp Gly Pro Arg Asp Met Pro Pro
                100                 105                 110

Gln Pro Tyr Lys Ile Tyr Glu Val Cys Ser Asn Gly Pro Ala Pro Thr
            115                 120                 125

Asp Ser Gln Pro Pro Glu Asp Tyr Ser Phe Gly Ala Gly Glu Glu Glu
    130                 135                 140

Glu Glu Glu Glu Glu Leu Gln Arg Met Leu Pro Ser Leu Ser Leu Thr
145                 150                 155                 160

Glu Asp Val Lys Trp Pro Pro Thr Leu Gln Pro Pro Thr Leu Arg Pro
                165                 170                 175

Pro Thr Leu Gln Pro Pro Thr Leu Gln Pro Val Val Leu Gly Pro
            180                 185                 190

Pro Ala Pro Asp Pro Ser Pro Leu Ala Pro Pro Gly Asn Pro Ala
    195                 200                 205

Gly Phe Arg Glu Leu Leu Ser Glu Val Leu Glu Pro Gly Pro Leu Pro
        210                 215                 220
```

```
Ala Ser Leu Pro Pro Ala Gly Glu Gln Leu Leu Pro Asp Leu Leu Ile
225                 230                 235                 240

Ser Pro His Met Leu Pro Leu Thr Asp Leu Glu Ile Lys Phe Gln Tyr
            245                 250                 255

Arg Gly Arg Pro Pro Arg Ala Leu Thr Ile Ser Asn Pro His Gly Cys
            260                 265                 270

Arg Leu Phe Tyr Ser Gln Leu Glu Ala Thr Gln Glu Gln Val Glu Leu
            275                 280                 285

Phe Gly Pro Ile Ser Leu Glu Gln Val Arg Phe Pro Ser Pro Glu Asp
        290                 295                 300

Ile Pro Ser Asp Lys Gln Arg Phe Tyr Thr Asn Gln Leu Leu Asp Val
305                 310                 315                 320

Leu Asp Arg Gly Leu Ile Leu Gln Leu Gln Gly Gln Asp Leu Tyr Ala
            325                 330                 335

Ile Arg Leu Cys Gln Cys Lys Val Phe Trp Ser Gly Pro Cys Ala Ser
            340                 345                 350

Ala His Asp Ser Cys Pro Asn Pro Ile Gln Arg Glu Val Lys Thr Lys
            355                 360                 365

Leu Phe Ser Leu Glu His Phe Leu Asn Glu Leu Ile Leu Phe Gln Lys
            370                 375                 380

Gly Gln Thr Asn Thr Pro Pro Phe Glu Ile Phe Phe Cys Phe Gly
385                 390                 395                 400

Glu Glu Trp Pro Asp Arg Lys Pro Arg Glu Lys Leu Ile Thr Val
                405                 410                 415

Gln Val Val Pro Val Ala Ala Arg Leu Leu Glu Met Phe Ser Gly
                420                 425                 430

Glu Leu Ser Trp Ser Ala Asp Ser Ile Arg Leu Gln Ile Ser Asn Pro
            435                 440                 445

Asp Leu Lys Asp Arg Met Val Glu Gln Phe Lys Glu Leu His His Ile
            450                 455                 460

Trp Gln Ser Gln Gln Arg Leu Pro Val Ala Gln Ala Pro Pro Gly
465                 470                 475                 480

Ala Gly Leu Gly Val Gly Gln Gly Pro Trp Pro Met His Pro Ala Gly
            485                 490                 495

Met Gln

<210> SEQ ID NO 9
<211> LENGTH: 503
<212> TYPE: PRT
<213> ORGANISM: Homo sapiens

<400> SEQUENCE: 9

Met Ala Leu Ala Pro Glu Arg Ala Ala Pro Arg Val Leu Phe Gly Glu
1               5                   10                  15

Trp Leu Leu Gly Glu Ile Ser Ser Gly Cys Tyr Glu Gly Leu Gln Trp
            20                  25                  30

Leu Asp Glu Ala Arg Thr Cys Phe Arg Val Pro Trp Lys His Phe Ala
        35                  40                  45

Arg Lys Asp Leu Ser Glu Ala Asp Ala Arg Ile Phe Lys Ala Trp Ala
    50                  55                  60

Val Ala Arg Gly Arg Trp Pro Pro Ser Ser Arg Gly Gly Gly Pro Pro
65                  70                  75                  80

Pro Glu Ala Glu Thr Ala Glu Arg Ala Gly Trp Lys Thr Asn Phe Arg
                85                  90                  95
```

```
Cys Ala Leu Arg Ser Thr Arg Arg Phe Val Met Leu Arg Asp Asn Ser
                100                 105                 110

Gly Asp Pro Ala Asp Pro His Lys Val Tyr Ala Leu Ser Arg Glu Leu
            115                 120                 125

Cys Trp Arg Glu Gly Pro Gly Thr Asp Gln Thr Glu Ala Glu Ala Pro
        130                 135                 140

Ala Ala Val Pro Pro Pro Gln Gly Gly Pro Pro Gly Pro Phe Leu Ala
145                 150                 155                 160

His Thr His Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
210                 215                 220

Ala Gly Gly Pro Gly Leu Pro Ala Gly Glu Leu Tyr Gly Trp Ala Val
225                 230                 235                 240

Glu Thr Thr Pro Ser Pro Gly Pro Gln Pro Ala Ala Leu Thr Thr Gly
                245                 250                 255

Glu Ala Ala Ala Pro Glu Ser Pro His Gln Ala Glu Pro Tyr Leu Ser
            260                 265                 270

Pro Ser Pro Ser Ala Cys Thr Ala Val Gln Glu Pro Ser Pro Gly Ala
        275                 280                 285

Leu Asp Val Thr Ile Met Tyr Lys Gly Arg Thr Val Leu Gln Lys Val
290                 295                 300

Val Gly His Pro Ser Cys Thr Phe Leu Tyr Gly Pro Pro Asp Pro Ala
305                 310                 315                 320

Val Arg Ala Thr Asp Pro Gln Val Ala Phe Pro Ser Pro Ala Glu
                325                 330                 335

Leu Pro Asp Gln Lys Gln Leu Arg Tyr Thr Glu Glu Leu Leu Arg His
            340                 345                 350

Val Ala Pro Gly Leu His Leu Glu Leu Arg Gly Pro Gln Leu Trp Ala
        355                 360                 365

Arg Arg Met Gly Lys Cys Lys Val Tyr Trp Glu Val Gly Gly Pro Pro
370                 375                 380

Gly Ser Ala Ser Pro Ser Thr Pro Ala Cys Leu Leu Pro Arg Asn Cys
385                 390                 395                 400

Asp Thr Pro Ile Phe Asp Phe Arg Val Phe Phe Gln Glu Leu Val Glu
                405                 410                 415

Phe Arg Ala Arg Gln Arg Arg Gly Ser Pro Arg Tyr Thr Ile Tyr Leu
            420                 425                 430

Gly Phe Gly Gln Asp Leu Ser Ala Gly Arg Pro Lys Glu Lys Ser Leu
        435                 440                 445

Val Leu Val Lys Leu Glu Pro Trp Leu Cys Arg Val His Leu Glu Gly
450                 455                 460

Thr Gln Arg Glu Gly Val Ser Ser Leu Asp Ser Ser Leu Ser Leu
465                 470                 475                 480

Cys Leu Ser Ser Ala Asn Ser Leu Tyr Asp Asp Ile Glu Cys Phe Leu
                485                 490                 495

Met Glu Leu Glu Gln Pro Ala
            500
```

```
<210> SEQ ID NO 10
<211> LENGTH: 504
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
aagcccaccg agaacaacga ggacttcaac atcgtggccg tggccagcaa cttcgccacc      60
accgacctgg acgccgatag gggcaaactg ccagggaaga agctgcccct ggaggtgctg     120
aaagagatgg aggccaacgc caggaaggcc ggctgcacaa gaggctgtct gatctgcctg     180
agccacatca agtgcacccc caagatgaag aagttcatcc ccggcaggtg tcacacctac     240
gagggcgaca agagagcgc ccagggcggc atcggcgagg ccatcgtgga catccccgag     300
atccccggct tcaaggacct ggagcccatg gagcagttca tcgcccaggt ggatctgtgc     360
gtggactgca ccaccggctg cctgaagggc ctggccaatg tgcaatgcag cgacctgctg     420
aagaaatggc tgccccagag gtgcgccacc ttcgccagca agatccaggg ccaagtggac     480
aagatcaagg gggctggggg ggac                                            504

<210> SEQ ID NO 11
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Lys Pro Thr Glu Asn Asn Glu Asp Phe Asn Ile Val Ala Val Ala Ser
1               5                   10                  15

Asn Phe Ala Thr Thr Asp Leu Asp Ala Asp Arg Gly Lys Leu Pro Gly
                20                  25                  30

Lys Lys Leu Pro Leu Glu Val Leu Lys Glu Met Glu Ala Asn Ala Arg
            35                  40                  45

Lys Ala Gly Cys Thr Arg Gly Cys Leu Ile Cys Leu Ser His Ile Lys
    50                  55                  60

Cys Thr Pro Lys Met Lys Lys Phe Ile Pro Gly Arg Cys His Thr Tyr
65                  70                  75                  80

Glu Gly Asp Lys Glu Ser Ala Gln Gly Gly Ile Gly Glu Ala Ile Val
                85                  90                  95

Asp Ile Pro Glu Ile Pro Gly Phe Lys Asp Leu Glu Pro Met Glu Gln
            100                 105                 110

Phe Ile Ala Gln Val Asp Leu Cys Val Asp Cys Thr Thr Gly Cys Leu
        115                 120                 125

Lys Gly Leu Ala Asn Val Gln Cys Ser Asp Leu Leu Lys Lys Trp Leu
    130                 135                 140

Pro Gln Arg Cys Ala Thr Phe Ala Ser Lys Ile Gln Gly Gln Val Asp
145                 150                 155                 160

Lys Ile Lys Gly Ala Gly Gly Asp
                165
```